United States Patent
Helle et al.

(10) Patent No.: US 9,726,591 B2
(45) Date of Patent: Aug. 8, 2017

(54) DUAL-FILTER DUAL-INTEGRITY TEST ASSEMBLY

(71) Applicant: MEDI-PHYSICS, INC., Princeton, NJ (US)

(72) Inventors: Kevin M Helle, Bartlett, IL (US); Michael T Schneider, Crystal Lake, IL (US)

(73) Assignee: General Electric Company, Schenectady, NY (US)

( * ) Notice: Subject to any disclaimer, the term of this patent is extended or adjusted under 35 U.S.C. 154(b) by 217 days.

(21) Appl. No.: 14/655,259

(22) PCT Filed: Dec. 26, 2013

(86) PCT No.: PCT/US2013/077794
§ 371 (c)(1),
(2) Date: Jun. 24, 2015

(87) PCT Pub. No.: WO2014/105946
PCT Pub. Date: Jul. 3, 2014

(65) Prior Publication Data
US 2015/0316462 A1    Nov. 5, 2015

Related U.S. Application Data

(60) Provisional application No. 61/746,187, filed on Dec. 27, 2012.

(51) Int. Cl.
*G01N 15/08* (2006.01)
*B01D 65/10* (2006.01)
*A61L 2/02* (2006.01)

(52) U.S. Cl.
CPC ............ *G01N 15/082* (2013.01); *A61L 2/022* (2013.01); *B01D 65/102* (2013.01); *G01N 2015/084* (2013.01)

(58) Field of Classification Search
CPC .............. B01D 65/102; B01D 2273/18; B01D 46/0012; G01N 15/0826; G01N 2015/086; G01N 2015/084; G01N 15/082
See application file for complete search history.

(56) References Cited

U.S. PATENT DOCUMENTS 3,765,225 A * 10/1973 Rivers ..................... G01M 3/20
                                                                73/40.7
4,494,403 A *  1/1985 Bowers ............. B01D 46/0006
                                                                73/40.7

(Continued)

FOREIGN PATENT DOCUMENTS

CN    101983158 A    3/2011
EP      1779913 A2    5/2007
(Continued)

OTHER PUBLICATIONS

Supplemental European Search Report regarding EP Application No. EP13867693, dated Jul. 22, 2016, 7 pages.
(Continued)

*Primary Examiner* — David A Rogers

(57) ABSTRACT

A dual-filter dual-integrity test conduit assembly allows for in-situ testing of both filters with separate, duplicate systems for membrane integrity so that if the first tester filter fails, the second filter may be tested with a different, but identical method with its own gauges and nitrogen supply so as to further isolate malfunctions of the filter integrity test equipment as a cause for erroneous batch failures.

18 Claims, 3 Drawing Sheets

(56) References Cited

U.S. PATENT DOCUMENTS

| | | | | |
|---|---|---|---|---|
| 4,515,007 A * | 5/1985 | Herman | ............... | G01M 3/20 55/DIG. 9 |
| 4,614,109 A * | 9/1986 | Hofmann | ............ | B01D 65/102 73/38 |
| 4,665,760 A * | 5/1987 | Eramo | ............... | G01N 15/0205 73/866.5 |
| 4,946,480 A * | 8/1990 | Hauville | ............... | B01D 46/10 55/320 |
| 5,353,630 A * | 10/1994 | Soda | ............... | B01D 65/102 73/38 |
| 5,507,959 A | 4/1996 | Glick | | |
| 5,591,898 A * | 1/1997 | Mayer | ............... | G01N 15/0826 73/38 |
| 5,685,991 A * | 11/1997 | Degen | ............... | B01D 65/102 210/500.41 |
| 6,324,898 B1 * | 12/2001 | Cote | ............... | B01D 65/102 210/90 |
| 6,568,282 B1 * | 5/2003 | Ganzi | ............... | B01D 65/102 73/38 |
| 6,666,970 B1 * | 12/2003 | Jornitz | ............... | B01D 65/102 210/138 |
| 6,983,504 B2 * | 1/2006 | Grummert | ............ | B01D 65/104 73/38 |
| 7,201,039 B2 * | 4/2007 | Morse | ............... | B01D 46/0086 73/38 |
| 7,246,515 B2 * | 7/2007 | Tyrell | ............... | B41J 2/16579 73/38 |
| 7,334,490 B2 * | 2/2008 | Morse | ............... | B01D 46/0086 73/38 |
| 7,592,178 B2 * | 9/2009 | Ding | ............... | B01D 65/102 422/122 |
| 7,677,084 B2 * | 3/2010 | Tyrell | ............... | B41J 2/16579 73/38 |
| 7,770,434 B2 * | 8/2010 | Brussermann | ............ | A61L 2/28 73/38 |
| 7,972,515 B1 * | 7/2011 | Mangum | ............... | B01D 65/104 210/321.65 |
| 8,518,166 B2 * | 8/2013 | Tasi | ............... | B01D 46/0086 55/385.2 |
| 8,689,610 B2 * | 4/2014 | Grant | ............... | B01D 65/102 73/38 |
| 8,881,600 B2 * | 11/2014 | Puppini | ............... | A61M 1/34 210/321.6 |
| 9,121,622 B2 * | 9/2015 | Dobbyn | ............... | B08B 15/023 |
| 2005/0092183 A1 | 5/2005 | Koslow et al. | | |
| 2009/0249895 A1 * | 10/2009 | Mahler | ............... | B01D 46/0086 73/863.23 |
| 2009/0298192 A1 * | 12/2009 | Parham | ............... | A62B 18/088 436/169 |
| 2010/0108591 A1 | 5/2010 | Wieczorek et al. | | |
| 2011/0067485 A1 * | 3/2011 | Grant | ............... | B01D 65/102 73/38 |
| 2011/0094619 A1 | 4/2011 | Steel et al. | | |
| 2011/0138936 A1 | 6/2011 | Collins et al. | | |
| 2011/0309275 A1 | 12/2011 | Azimi et al. | | |
| 2012/0059603 A1 | 3/2012 | Stering | | |

FOREIGN PATENT DOCUMENTS

| | | |
|---|---|---|
| EP | 1849484 A1 | 10/2007 |
| WO | 00/50158 A1 | 8/2000 |
| WO | 02/066099 A | 8/2002 |
| WO | 2007080260 | 7/2007 |
| WO | 2009100428 A1 | 8/2009 |

OTHER PUBLICATIONS

International Search Report and Written Opinion for International Application No. PCT/US2013/077794, mail date Apr. 24, 2014, 11 pages.

* cited by examiner

US 9,726,591 B2

DUAL-FILTER DUAL-INTEGRITY TEST ASSEMBLY

This application is a filing under 35 U.S.C. 371 of international application number PCT/US2013/077794, filed Dec. 26, 2013, which claims priority to U.S. application No. 61/746,187, filed Dec. 27, 2012, the entire disclosures of each of which are hereby incorporated by reference.

FIELD OF THE INVENTION

The present invention relates to the field of quality control. More specifically, the present invention is directed to systems and methods for ensuring quality of dispensed fluids.

BACKGROUND OF THE INVENTION

The last step of an aseptic terminal dispensing operation is to pass the product fluid through a filter. As the filtering is a critical-to-quality step, the filter must be tested once dispensing is complete to ensure the integrity of the filter media and thus the quality of the dispensed product. Testing of the filter media is performed by having a pressurized nitrogen source, through a burst line, apply pressure on the filter. Pressure above the filter, ie, on the same side of the filter media as the product fluid source, as well as pressure below the filter, ie, on the same side of the filter media as the dispensed product, is measured and recorded. Should the pressure below the filter suddenly increase, the integrity of the filter will be known to have failed. The filter must be kept wet during the integrity testing, or there is a risk of air-lock occurring which will thwart the testing. In one test method, Bubble Point Testing, the pressure at which the membranes fail and nitrogen bubbles are visible in transparent conduits downstream of the filter is provided by visual confirmation.

The integrity test is always performed to destruction. The burst pressure, or in a Bubble Point Test the pressure reading at which the membranes fail and nitrogen bubbles are visible downstream of the filter, for the filter is recorded. If the burst pressure, or bubble point, exceeds the minimum reading, the filter membrane can be considered intact for the fill. However, should the burst pressure be too low, or the pressure recorded below the filter be too high for a given burst pressure applied above the filter, the filter will be deemed to have been defective and the dispensed fluid will be deemed to have failed quality control. It is impermissible under regulations to simply then run the failed fluid through a new filter, as that is considered re-compounding. The loss of the dispensed product fluid may thus be extremely costly. And because the loss of the dispensed product fluid is so costly, producers must be sure of the quality of the dispensed product, and thus the integrity of the filters used in the final dispense step. Also of concern is the possibility of false failures, which will also result in loss of the dispensed fluid.

To reduce risk of losing the dispensed liquid, and with reference to FIG. 1, a secondary filter 2 is often included in the dispense procedure, where the secondary filter is serially connected directly to the primary filter 1. If the primary filter fails the destructive burst test, the secondary filter may be tested so that if it passes, the disposition of the dispensed product liquid is improved. However, as this testing takes place after removal of both filters 1 and 2 from the dispense line, and employs a common test method, ie, line, valving, $N_2$ burst gas supply, burst regulator, are used for both filters 1 and 2. Differentiation between the filter integrity and the test method are not always clear as one cannot be sure that it was the test method equipment or the filters which are defective. The art lacks a system or method for allowing filter integrity testing of two filters serially connected along a dispense path.

DETAILED DESCRIPTION OF THE PREFERRED EMBODIMENTS

Figure 1:
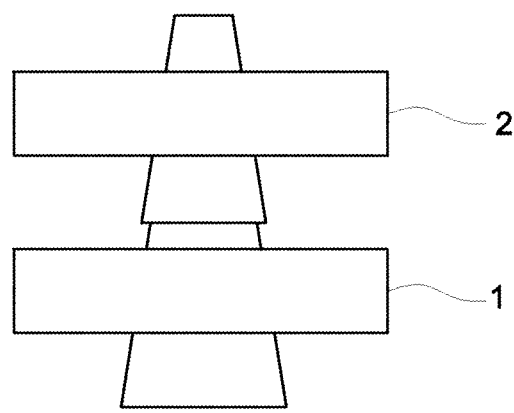
FIG. 1 depicts the serial connection between a primary filter and a secondary filter as is typically used in dispense systems of the prior art.

The present invention provides a dual-filter dual-integrity test conduit assembly and method which provides for individual in-situ testing of the two filters use for dispensing product liquids. Desirably, the proposed method allows for in-situ testing of both filters with separate, duplicate systems for membrane integrity. Thus, if the primary filter fails its integrity test, the secondary filter may be tested the second filter with a different, but identical method with its own gauges and nitrogen supply. This configuration rules out the filter integrity test equipment as a cause for erroneous batch failures. Desirably, the assembly of the present invention is connected to two independent burst gas reservoirs and uses two different sets of regulators for testing each filter. It is contemplated that a single burst gas reservoir may be employed, however it is desirable to use two independent integrity test circuits so that no single failure would cause both integrity circuits to provide an erroneous reading on either side of a filter membrane.

If a single burst gas supply is used, the present invention would switch the primary and secondary filters so that the primary filter is positioned to first filter the product fluid, as it is common to provide the primary filter further downstream than the secondary filter. In the single burst gas supply configuration, the primary filter will be in a position to be tested before the secondary filter, such that failure of the primary filter may be performed prior to failure of the secondary filter.

The dual-filter dual-integrity test conduit assembly of the present invention may be provided as a disposable kit, desirably pre-assembled. Additionally, the present invention may be provided in a container or bag in a sterile condition such that it may be removed from the container in a sterile or environmentally-controlled environment so that it may be directly connected between a source of a product fluid, a dispense container for the product fluid, sources of burst gas and to waste containers. For example, the assembly may be sterilized and provided within a container meeting class 100 conditions. While the assembly need not be sterile for a terminally-sterilized product, it is required for aseptic dispense operations. The bags providing the assembly of the present invention may be multi-layer bags including one or more elastomeric layers or one or more metallic layers.

The valves of the present invention may be set, or ratcheted, manually, although the valves are contemplated to be automatically operated by other machinery. Additionally, the pressure transducers of the present invention provide indicia of pressure to one side of their respective filter membranes. The pressures indicated by each transducer may be manually recorded, although the present invention contemplates that the pressure transducers may themselves be connected or read by recording equipment for providing a record of the pressures at each valve over time. Batch records for each transducer are recorded and the readings are compared to reference standards to ensure the membranes have performed as required for a dispense operation.

It is important that the filter membranes remain wet after use (dispensing) and through testing, or it will air lock. As the length and volume of the fluid lines, as well as the starting bulk volume are known, one may determine how much fluid should be in the assembly of the present invention. In a desired embodiment, fluid within the assembly may be confirmed by visual inspection of the transparent conduit lines.

Figure 2:
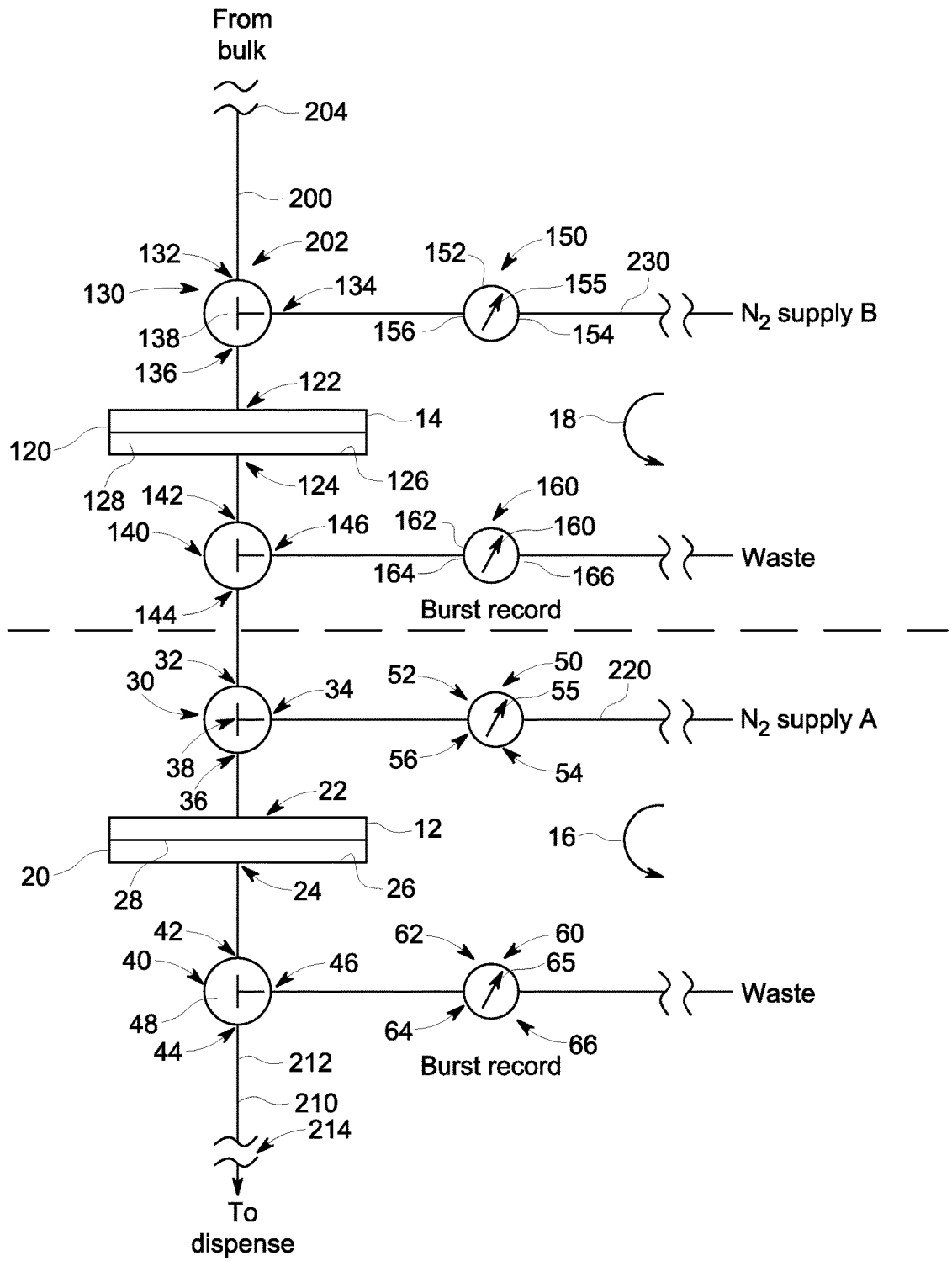
FIG. 2 depicts a schematic of a dual filter dual integrity assembly of the present invention.
Figure 3:
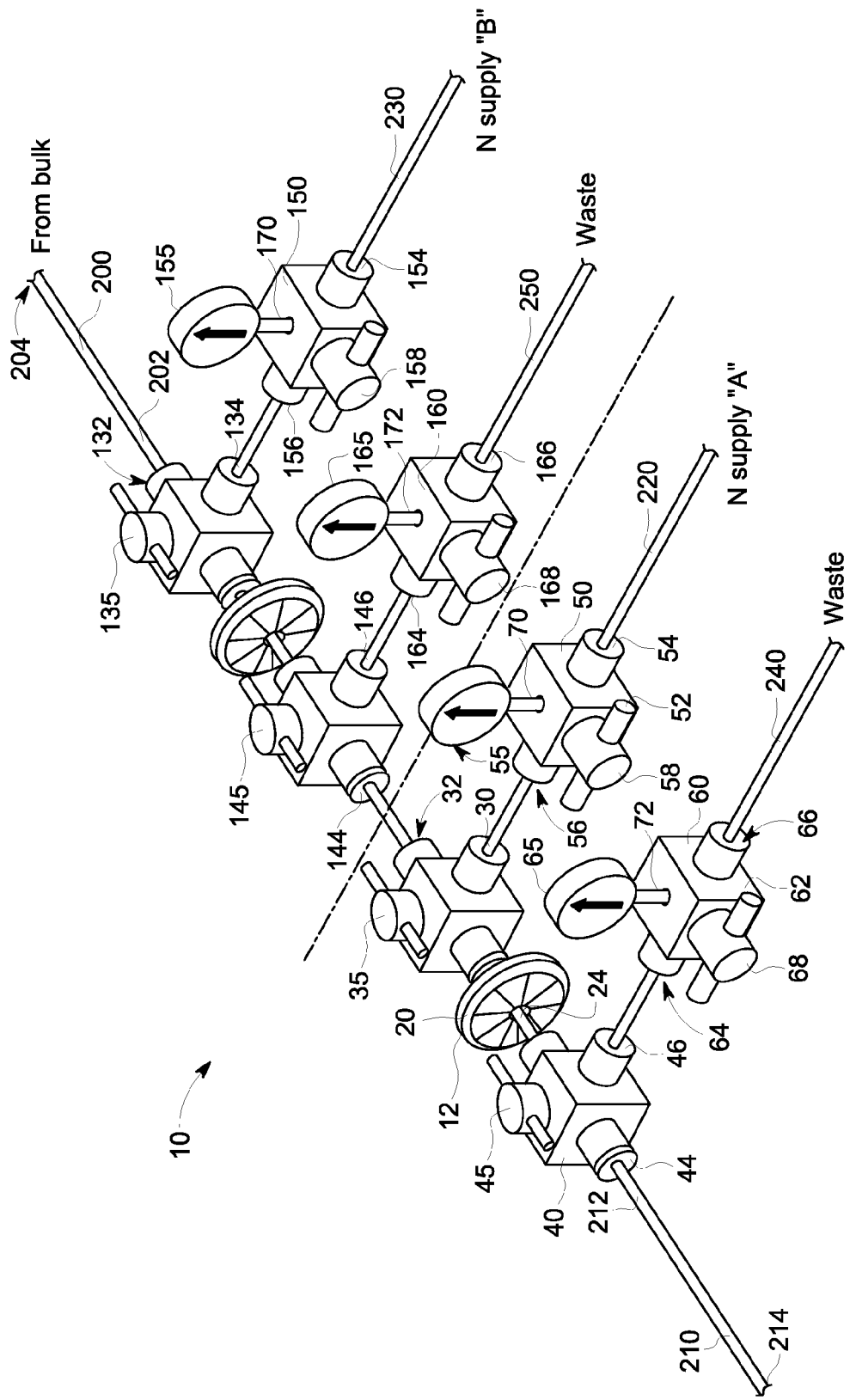
FIG. 3 is an alternate depiction of the dual filter dual integrity assembly of the present invention.

Referring to FIGS. 2 and 3, the present invention provides a dual filter dual integrity test conduit assembly 10. Assembly 10 provides first, or primary, and second, or secondary, filter units 12 and 14, respectively, arranged for serial-flow of a product fluid from a bulk source (not shown) to a dispense container (not shown) while also providing for individual in-situ burst testing of primary filter unit 12 and secondary filter unit 14.

Assembly 10 provides a first filter integrity test circuit 16 having primary filter unit 12. As used herein, the term 'circuit' does not indicate a circular flow path for a fluid, but is denotes the flowpath for a burst gas which partially coincides with a portion of a fluid flowpath between a bulk container and a filtrate container. Primary filter unit 12 includes a filter housing 20 defining an entry port 22, an exit port 24, and a filter cavity 26 in fluid communication therebetween. A filter membrane 28 spans filter cavity 26 such that filter membrane 28 provides filtered isolation between entry port 22 and exit port 24. Filter unit 12 is desirably a dead-end filters employing a hydrophilic membrane having a pore size of about 0.2-0.22 microns, such as a Medical Millex-GP Filter Unit, catalogue number SLGPM33RS, sold by EMD Millipore Corporation of Billerica, Mass.

Circuit 16 further includes a first upstream valve 30 having first and second input ports 32 and 34, respectively, and an output port 36. First and second input ports 32 and 34 are each individually in selectable fluid communication with output port 36. That is, valve 30 includes a fluid-directing mechanism 38, such as a stopcock 35 which is movable between a first position placing first input port 32 in fluid communication with output port 36 while fluidly isolating second input port 34 from out port 26, and a second position placing second input port 34 in fluid communication with output port 36 while fluidly isolating first input port 32 from output port 36. Output port 36 of first upstream valve 30 is placed in fluid communication with entry port 22 of first filter unit 12.

Circuit 16 further includes a first downstream valve 40 having an input port 42 and first and second output ports 44 and 46, respectively. First and second output ports 44 and 46 are each individually in selectable fluid communication with input port 42. That is, valve 40 includes a fluid-directing mechanism 48, such as a stopcock 45 which is movable between a first position placing input port 42 in fluid communication with first output port 44 while fluidly isolating second output port 46 from input port 42, and a second position placing input port 42 in fluid communication with second output port 46 while fluidly isolating first output port 44 from input port 42. Input port 42 of valve 40 is placed in fluid communication with exit port 24 of first filter unit 12.

Circuit 16 further includes a first and second integrity valve 50 and 60, respectively. Valves 50 and 60 are desirably in the form of pneumatic pressure regulating valves which provide a controller for variably opening and closing the valve as well as a pressure transducer which provides an indication of the pressure within its respective valve. The present invention further contemplates that valves 50 and 60 may be replaced solely by pressure gages when opening and closing of a burst gas supply is performed solely at the burst gas tank or reservoir. Desirably, both valve 50 and 60 include a gage 55 and 65 which translate the signal from its internal transducer into a reading of the pressure in each valve. Alternatively, the present invention contemplates that the internal transducers may provide a signal to a remote station for reading the pressure. That is, the transducers may be electromechanical devices or strain gages which can provide an electrical signal corresponding to the pressure within the valve. With valves 30 and 40 properly set, the transducers will be able to measure the pressure on each side of filter membrane 28.

Valves 50 and 60 each include a valve body 52 and 62 with an input port 54 and 64 and an output port 56 and 66, respectively. Valves 50 and 60 further include a shunt mechanism or actuator 58 and 68, respectively, moveable between a first position providing fluid communication between input port 54 and 64 and output port 56 and 66, respectively, and a second position fluidly isolating input port 54 and 64 from output port 56 and 66, respectively. Actuators 58 and 68 desirably provide for continuous or stepped settings so as to allow a user to set the actuator between the first and second positions. Output port 56 of first integrity valve 50 is placed in fluid communication with second input port 34 of first upstream valve 30 and input port 62 of second integrity valve 60 is placed in fluid communication with second output port 46 of first downstream valve 40.

In FIG. 3, valve 50 is shown to include a first pressure transducer 70 operably connected thereto. Valve 60 is shown to include a second pressure transducer 72 operably connected thereto. The present invention contemplates that when the fluid-directing mechanism 38 of valve 30 is set in the second position and the fluid-directing mechanism 48 of valve 40 is set to the second position, then transducers 70 and 72 will detect the fluid pressure on either side of membrane 28 in filter unit 12. That is, transducer 70 will provide a pressure reading for the flowpath between output port 56 and membrane 28 while transducer 72 may provide a pressure reading for the flowpath between membrane 28 and input port 64 of valve 60.

Assembly 10 also provides a second filter integrity test circuit 18, independent of first filter integrity test circuit 16. Circuit 18 includes secondary filter unit 14. Secondary filter unit 14 includes a filter housing 120 defining an entry port 122, an exit port 124, and a filter cavity 126 in fluid communication therebetween. A filter membrane 128 spans filter cavity 126 such that filter membrane 128 provides filtered isolation between entry port 122 and exit port 124. Filter unit 14 is desirably a dead-end filter employing a hydrophilic membrane having a pore size of about 0.2-0.22 microns, such as a Medical Millex-GP Filter Unit, catalogue number SLGPM33RS, sold by EMD Millipore Corporation of Billerica, Mass.

Circuit 18 further includes a second upstream valve 130 having first and second input ports 132 and 134, respectively, and an output port 136. First and second input ports 132 and 134 are each individually in selectable fluid communication with output port 136. That is, valve 130 includes a fluid-directing mechanism 138, such as a stopcock 135 which is movable between a first position placing first input port 132 in fluid communication with output port 136 while fluidly isolating second input port 134 from out port 126, and a second position placing second input port 134 in fluid communication with output port 136 while fluidly isolating first input port 132 from output port 136. Output port 136 of first upstream valve 130 is placed in fluid communication with entry port 122 of first filter unit 12.

Circuit 18 further includes a second downstream valve 140 having an input port 142 and first and second output ports 144 and 146, respectively. First and second output ports 144 and 146 are each individually in selectable fluid communication with input port 142. That is, valve 140 includes a fluid-directing mechanism 148, such as a stopcock 145 which is movable between a first position placing input port 142 in fluid communication with first output port 144 while fluidly isolating second output port 146 from input port 142, and a second position placing input port 142 in fluid communication with second output port 146 while fluidly isolating first output port 144 from input port 142. Input port 142 of valve 140 is placed in fluid communication with exit port 124 of second filter unit 14. Additionally, exit port 124 of valve 140 is placed in fluid communication with input put port 42 of valve 40.

Circuit 18 further includes a third and fourth integrity valve 150 and 160, respectively. Valves 150 and 160 are desirably in the form of pneumatic pressure regulating valves which provide a controller for variably opening and closing the valve as well as a pressure transducer which provides an indication of the pressure within its respective valve. The present invention further contemplates that valves 150 and 160 may be replaced solely by pressure gages when opening an closing of a burst gas supply is performed solely at the burst gas tank or reservoir. Desirably, both valve 150 and 160 include a gage 155 and 165 which translate the signal from its internal transducer into a reading of the pressure in each valve. Alternatively, the present invention contemplates that the internal transducers may provide a signal to a remote station for reading the pressure. That is, the transducers may be electromechanical devices or strain gages which can provide an electrical signal corresponding to the pressure within the valve. With the fluid-directing mechanisms of valves 130 and 140 properly set, the transducers will be able to measure the pressure on each side of filter membrane 128 in secondary filter unit 14.

Valves 150 and 160 each include a valve body 152 and 162 with an input port 154 and 164 and an output port 156 and 166, respectively. Valves 150 and 160 further include a shunt mechanism or actuator 158 and 168, respectively, moveable between a first position providing fluid communication between input port 154 and 164 and output port 156 and 166, respectively, and a second position fluidly isolating input port 154 and 164 from output port 156 and 166, respectively. Actuators 158 and 168 desirably provide for continuous or stepped settings so as to allow a user to set the actuator between the first and second positions. Output port 156 of third integrity valve 150 is placed in fluid communication with second input port 134 of second upstream valve 130 and input port 162 of fourth integrity valve 160 is placed in fluid communication with second output port 146 of second downstream valve 140.

In FIG. 3, valve 150 is shown to include a first pressure transducer 170 operably connected thereto. Valve 160 is shown to include a second pressure transducer 172 operably connected thereto. The present invention contemplates that when the fluid-directing mechanism 138 of valve 130 is set in the second position and the fluid-directing mechanism 148 of valve 140 is set to the second position, then transducers 170 and 172 will detect the fluid pressure on either side of membrane 128 in filter unit 14. That is, transducer 70 will provide a pressure reading for the flowpath between output port 156 and membrane 128 while transducer 172 may provide a pressure reading for the flowpath between membrane 128 and input port 164 of valve 160.

Assembly 10, desirably includes an elongate bulk conduit 200 connected at first input port 132 at a first end 202. By connecting the opposite end 204 of conduit 200 in a source of bulk product liquid, input port 132 will be in fluid communication bulk liquid container cavity which provides a bulk liquid to valve 130. With the fluid-directing mechanisms of valves 30, 40, 130 and 140 in the first position, the product liquid may be directed from the bulk container, through the secondary and then the primary filters 14 and 12, respectively, then out the first output port 44 of valve 40. Desirably, assembly 10 includes an elongate filtrate conduit 210 connected at output port 44 at a first end 212. Opposing end 214 of conduit 210 is provided at a dispense vial or container so as to direct the product fluid post-filtration therein. It is contemplated that opposing end 214 supports a fitting for connection to a mating fitting associated with the dispense vial. Alternatively, it is contemplated that end 214 may support an elongate fill needle for puncturing through a septum of a dispense vial.

The present invention further contemplates that elongate supply conduits 220 and 230 are connected to the input ports of valves 50 and 150 and that elongate burst conduits 240 and 250 are connected to output ports of valves 60 and 160, respectively. The free ends of conduits 220 and 230 are connectable to a source of burst gas, such as a tank of nitrogen gas. The free ends of conduits 240 and 250 are connectable or cooperative with a waste receptacle or other waste line. The present invention contemplates that other conduit segments may be used to connect the valves and filters of the present invention so that their ports are in fluid communication as described above.

Each of the conduit sections of assembly 10 shown in FIG. 3 are desirably formed from a polymeric tubing suitable for the purposes of dispensing the product fluid. Additionally, the present invention contemplates that communication between each of the ports as described herein may be achieved by connecting segments of similar conduit tubing between the communicating ports (such segments are not called out herein but are contemplated to be employed in one embodiment of the present invention). By way of illustration and not of limitation, the conduits may be formed from PTFE tubing. The motive force for directing a product fluid from the bulk container through assembly 10 is contemplated to be provided by any suitable means, including by way of illustration and not of limitation, a peristaltic pump which acts upon bulk conduit 200 such as the REPEATER Pump model 099E sold by Baxa Corporation of Englewood, Colo. Alternatively, it is contemplated that the motive force may be provided by any suitable pump or displacement mechanism which can accommodate assembly 10.

Valves 30, 40, 130 and 140 are desirably three-port (three position)/two-way-disposable valves formed from a suitable polymeric material, particularly for disposable versions of assembly 10, although any suitable material is contemplated by the present invention. One example of a valve for these purposes is the model MX2311L ULTRA™ 3-way stopcock w/swivel male luer lock 50/CA sold by SMITHS MEDICAL of St. Paul, Minn.

In another embodiment, the present invention provides a disposable kit for dispensing a product fluid. The kit desirably includes the serially-arranged filter units 12 and 14, valves 30, 40, 130 and 140 as well as conduits 200 and 210 pre-assembled. The kit is adaptable to be connected at ports 34 and 134 to conduits communicating with separate burst gas supply sources and at ports 46 and 146 to conduits communicating with a waste receptacle. It is contemplated that for this embodiment of the invention, the burst gas sources will provide along their respective lines a means for stepping up and displaying the burst gas pressure being applied to the membranes of filter units 12 and 14. Additionally, it is contemplated for this embodiment that the conduits communicating with the waste receptacles will include means for displaying the pressure experienced downstream of each filter unit membrane. In this embodiment, the user may use their own calibrated gages for recording the pressures on either side of membranes 28 and 128. In yet still another embodiment, the present invention provides this same kit with conduits having one end connected to ports 34, 46, 134, and 146 for connection to pressure gages provided for their respective burst gas supply or waste line pressure readings. This alternate embodiment of a kit of the present invention thus provides for connection to valves or gages which are calibrated and re-used for each dispensing operation.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A dual filter dual integrity test conduit assembly comprising:
    A first filter unit comprising a filter housing defining an entry port, an exit port, and a filter cavity in fluid communication therebetween, a filter membrane spanning said filter cavity such that said filter membrane provides filtered isolation between said entry port and said exit port;
    A second filter unit comprising a filter housing defining an entry port, an exit port, and a filter cavity in fluid communication therebetween, a filter membrane spanning said filter cavity such that said filter membrane provides filtered isolation between said entry port and said exit port;
    First and second upstream valves, each of said first and second upstream valves including a valve body defining a first and second input port and an output port, each said first and second upstream valve further including a stopcock movable between a first position placing said first input port in fluid communication with said output port while fluidly isolating said second input port from said out port and a second position placing said second input port in fluid communication with said output port while fluidly isolating said first input port from said output port, wherein said output port of said first upstream valve is placed in fluid communication with said input port of said first filter and said output port of said second upstream valve is placed in fluid communication with said input port of said second filter;
    First and second downstream valves, each of said first and second downstream valves including a valve body defining an input port and a first and second output port, each said first and second downstream valve further including a stopcock movable between a first position placing said first input port in fluid communication with said first output port while fluidly isolating said second output port and a second position placing said input port in fluid communication with said second output port while fluidly isolating said first output port, wherein said input port of said first downstream valve is placed in fluid communication with said output port of said first filter and said input port of said second downstream valve is placed in fluid communication with said output port of said second filter, and wherein said first input port of said second upstream valve is placed in fluid communication with said first output port of said first downstream valve; and
    First, second, third, and fourth integrity valves each comprising valve body with an input port and an output port, each said integrity valve including a shunt mechanism moveable between a first position providing fluid communication between said input port and said output port and a second position fluidly isolating said input port from said output port, wherein said output ports of said first, second, third, and fourth integrity valves are placed in fluid communication with said second input port of said first upstream valve, said second output port of said first downstream valve, said second input port of said second upstream valve and said second output port of said second downstream valve, respectively.

2. An assembly of claim 1, wherein each said upstream and downstream valve is a three-way valve including a stopcock rotatable between said first and second positions.

3. An assembly of claim 1, further comprising an elongate hollow bulk conduit having one end connected to said first input port of said first upstream valve.

4. An assembly of claim 3, wherein the opposite end of said bulk conduit is adapted to be connected to a source of bulk liquid to be dispensed through said first and second filters.

5. An assembly of claim 3, further comprising an elongate hollow dispense conduit having one end connected to said output port of said second downstream valve.

6. An assembly of claim 5, wherein the opposite end of said dispense conduit is adapted to be connected to a dispense container for said bulk liquid after passing through said first and second filters.

7. An assembly of claim 1, further comprising a first, second, third, and fourth elongate hollow conduit connected to said input port of said first, second, third, and fourth integrity valve, respectively.

8. An assembly of claim 1, further comprising a first, second, third, and fourth elongate hollow deflectable burst conduit including opposed first and second open ends and an elongate hollow conduit body extending therebetween, wherein said first ends are connected in fluid communication with said second input port of said first upstream valve, said second output port of said first downstream valve, said second input port of said second upstream valve and said second output port of said second downstream valve, respectively.

9. An assembly of claim 1, wherein each of said integrity valves further comprises a pressure transducer operably connected to determine the fluid pressure within each said integrity valve.

10. An assembly of claim 1, provided in the sealed cavity of a sterile bag.

11. An assembly of claim 10, wherein said bag is provided within the sealed cavity of a second sterile bag.

12. An assembly of claim 11, wherein each said cavity of said first and second bags provides an environment meeting class 100 standard.

13. An assembly of claim 11, wherein each of said first and second bags comprise an elastomeric layer.

14. An assembly of claim 11, wherein at least one of said first and second bags comprise a metallic layer.

15. A dual-filter dual-integrity test conduit assembly comprising:
   A first filter integrity test circuit comprising:
      A first filter unit comprising a filter housing defining an entry port, an exit port, and a filter cavity in fluid communication therebetween, a filter membrane spanning said filter cavity such that said filter membrane provides filtered isolation between said entry port and said exit port;
      A first upstream valve having a first and second input ports and an output port, said first and second input ports individually in selectable fluid communication with said output port, wherein said output port is in fluid communication with said entry port of said first filter unit;
      A first downstream valve having a an input port and first and second output ports, said first and second output ports individually in selectable fluid communication with said input port of said first downstream valve,
      A first and second integrity valve each comprising valve body with an input port and an output port, each said integrity valve including a shunt mechanism moveable between a first position providing fluid communication between said input port and said output port and a second position fluidly isolating said input port from said output port, wherein said output ports of said first integrity valve is placed in fluid communication with said second input port of said first upstream valve and said input port of said second integrity valve is placed in fluid communication with said second output port of said first downstream valve;
      a first pressure transducer operably connected to determine the fluid pressure between said entry port and said membrane of said first valve unit; and
      a second pressure transducer operably connected to determine the fluid pressure between said exit port and said membrane of said first valve unit;
   A second filter integrity test circuit, independent of said first filter integrity test circuit comprising:
      A second filter unit comprising a filter housing defining an entry port, an exit port, and a filter cavity in fluid communication therebetween, a filter membrane spanning said filter cavity such that said filter membrane provides filtered isolation between said entry port and said exit port;
      A second upstream valve having a first and second input ports and an output port, said first and second input ports individually in selectable fluid communication with said output port, wherein said output port is in fluid communication with said entry port of said second filter unit;
      A second downstream valve having an input port and first and second output ports, said first and second output ports individually in selectable fluid communication with said input port of said second downstream valve,
      A third and fourth integrity valve each comprising valve body with an input port and an output port, each said integrity valve including a shunt mechanism moveable between a first position providing fluid communication between said input port and said output port and a second position fluidly isolating said input port from said output port, wherein said output ports of said third integrity valve is placed in fluid communication with said second input port of said second upstream valve and said input port of said fourth integrity valve is placed in fluid communication with said second output port of said second downstream valve;
      a third pressure transducer operably connected to determine the fluid pressure between said entry port and said membrane of said second valve unit; and
      a fourth pressure transducer operably connected to determine the fluid pressure between said exit port and said membrane of said second valve unit;
   wherein said first output port of said first downstream valve is in fluid communication with said input port of said second upstream valve so that said outlet port of said first filter is in selectable fluid communication with said inlet port of said second filter for dispensing of a product liquid through said first and second filters.

16. A dual-filter dual-integrity test conduit assembly of claim 15, wherein at least one of said upstream or downstream valves further comprise a stopcock movable between a first position placing said first input port in fluid communication with said output port while fluidly isolating said second input port from said output port and a second position placing said second input port in fluid communication with said output port while fluidly isolating said first input port from said output port.

17. A dual-filter dual-integrity test conduit assembly of claim 15, wherein said first, second, third, and fourth pressure transducers are integral with said first, second, third, and fourth integrity valves, respectively.

18. A method for dispensing a product liquid comprising the steps of:
   directing a product liquid into a first conduit, and
   in-situ testing the integrity of the first filter after the product liquid has been dispensed, said testing step further comprising the steps of directing a burst gas against a disposable dual-filter dual-integrity test conduit as in either claim 1 or claim 15.

* * * * *